(12) United States Patent
Ahlers

(10) Patent No.: US 6,835,855 B2
(45) Date of Patent: Dec. 28, 2004

(54) METAL COMPLEX CARRYING A 2-PHOSPA-TRICYCLO[3.3.1.1(3.7)]DECYL RADICAL AS A LIGAND IN HYDROFORMYLATION

(75) Inventor: Wolfgang Ahlers, Worms (DE)

(73) Assignee: BASF Aktiengesellschaft, Ludwigshafen (DE)

(*) Notice: Subject to any disclaimer, the term of this patent is extended or adjusted under 35 U.S.C. 154(b) by 92 days.

(21) Appl. No.: 10/275,562

(22) PCT Filed: May 11, 2001

(86) PCT No.: PCT/EP01/05405

§ 371 (c)(1),
(2), (4) Date: Nov. 7, 2002

(87) PCT Pub. No.: WO01/85661

PCT Pub. Date: Nov. 15, 2001

(65) Prior Publication Data

US 2003/0092935 A1 May 15, 2003

(30) Foreign Application Priority Data

May 12, 2000 (DE) .......................... 100 23 468

(51) Int. Cl.$^7$ ........................ C07C 45/50; C07F 9/00
(52) U.S. Cl. .................. 568/454; 568/452; 568/457; 556/20
(58) Field of Search ................. 568/454, 457, 568/452; 556/20

(56) References Cited

U.S. PATENT DOCUMENTS 3,050,531 A * 8/1962 Epstein et al.
6,037,500 A * 3/2000 Zhang

FOREIGN PATENT DOCUMENTS

| GB | 1 573 422 | 8/1980 |
|----|-----------|--------|
| WO | 98/42717 | 10/1998 |

OTHER PUBLICATIONS

XP–001010653, Gee et al. CHem.Comm.1999,901–902.
Organometallics 2000, 19, 2791–3796 XP–002173920, Carraz et al.

* cited by examiner

Primary Examiner—Johann Richter
Assistant Examiner—Sikarl A. Witherspoon
(74) Attorney, Agent, or Firm—Keil & Weinkauf

(57) ABSTRACT

In a process for the hydroformylation of ethylenically unsaturated compounds, at least one ethylenically unsaturated compound is reacted with carbon monoxide and hydrogen in the presence of a ligand-metal complex of ruthenium, rhodium, palladium, iridium and/or platinum, where the ligand-metal complex comprises a monophosphine, monophosphinite or monophosphinamidite ligand of the formula I

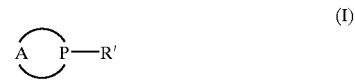

(I)

where

A together with the phosphorus atom to which it is bound forms a 2-phosphatricyclo[3.3.1.1{3,7}]decyl radical in which one or more nonadjacent carbon atoms may be replaced by heteroatoms and which may be substituted, and R' is hydrogen or an organic radical having a molecular weight of up to 20 000 bound via a carbon atom or oxygen atom or nitrogen atom.

The process is particularly useful for the hydroformylation of internal branched olefins and lower pressures and/or temperatures are required in the hydroformylation than when using other phosphorus ligands.

6 Claims, No Drawings

METAL COMPLEX CARRYING A 2-PHOSPA-TRICYCLO[3.3.1.1(3.7)]DECYL RADICAL AS A LIGAND IN HYDROFORMYLATION

This application is a 371 of PCT/EP01/05404 filed May 11, 2001.

The present invention relates to a process for the hydroformylation of ethylenically unsaturated compounds, in which at least one ethylenically unsaturated compound is reacted with carbon monoxide and hydrogen in the presence of a ligand-metal complex of ruthenium, rhodium, palladium, iridium and/or platinum, and to a ligand-metal complex suitable for the process.

Hydroformylation or the oxo process is an important industrial process and is used for preparing aldehydes by reaction of ethylenically unsaturated compounds with carbon monoxide and hydrogen. The reaction itself is strongly exothermic and generally proceeds under superatmospheric pressure and elevated temperatures in the presence of catalysts. In industrial practice, cobalt catalysts were first employed, but rhodium catalysts now predominate. To stabilize the rhodium-containing catalyst during the reaction and to avoid decomposition of the catalyst with precipitation of metallic rhodium during the work-up, phosphorus-containing ligands are generally used as cocatalysts. In the case of lower α-olefins, the use of triphenylphosphine and other triarylphosphines, in particular, as cocatalysts has proven useful (cf., for example, J. Falbe, New Synthesis with Carbonmonoxide, Springer, Berlin, 1980, p. 55ff). Although lower α-olefins can be hydroformylated very well using triarylphosphine-modified rhodium catalysts, this catalyst system is not very suitable for internal and internal branched olefins and for higher α-olefins. Thus, internal and internal branched double bonds are hydroformylated only very slowly in the presence of such a catalyst. For this reason, the hydroformylation of substrates having internal and/or internal branched double bonds requires use of high pressures and/or temperatures.

WO 98/42717 describes carbonylation reactions in the presence of diphosphines in which at least one phosphorus atom is part of a 2-phosphatricyclo[3.3.1.1{3,7}]decyl group.

FR 118524 describes, inter alia, the hydroformylation of olefinic compounds in the presence of a cobalt carbonyl catalyst and a cocatalyst in the form of a trioxaphosphaadamantane.

It is an object of the present invention to provide a process for the hydroformylation of ethylenically unsaturated compounds in the presence of a ligand-metal complex of ruthenium, rhodium, palladium, iridium and/or platinum as catalyst, by means of which ethylenically unsaturated compounds, in particular ethylenically unsaturated compounds having internal and/or internal branched double bonds can be reacted under pressure and/or temperature conditions which are as mild as possible.

We have found that this object is achieved by a process for the hydroformylation of ethylenically unsaturated compounds, in which at least one ethylenically unsaturated compound is reacted with carbon monoxide and hydrogen in the presence of a ligand-metal complex of ruthenium, rhodium, palladium, iridium and/or platinum, where the ligand-metal complex comprises a monophosphine, monophosphinite or monophosphinamidite ligand of the formula I

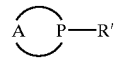

(I)

where

A together with the phosphorus atom to which it is bound forms a 2-phosphatricyclo[3.3.1.1{3,7}]decyl radical in which one or more nonadjacent carbon atoms may be replaced by heteroatoms and which may be substituted, and R' is hydrogen or an organic radical having a molecular weight of up to 20 000 bound via a carbon atom or oxygen atom or nitrogen atom.

In addition, the invention provides a metal-ligand complex comprising a metal selected from among ruthenium, rhodium, palladium, iridium and/or platinum and at least one monophosphine or monophosphinite ligand as defined above.

It has been found that ethylenically unsaturated compounds, in particular those having internal branched double bonds, can be reacted by means of the process of the present invention at significantly lower temperatures and/or pressures than those required for the hydroformylation of the same substrates using the same catalytically active metal but other phosphorus-containing cocatalysts, e.g. triarylphosphines. In particular, the process of the present invention makes it possible to hydroformylate ethylenically unsaturated compounds, in particular those having internal branched double bonds, at pressures of less than 100 bar, preferably less than 80 bar.

Tricyclo[3.3.1.1{3,7}]decane is also known under the trivial name "adamantane". In the 2-phosphatricyclo[3.3.1.1{3,7}]decyl radical of the ligand used according to the present invention, one or more nonadjacent carbon atoms, which are preferably not adjacent to the phosphorus atom, may be replaced by heteroatoms, preferably oxygen atoms and/or nitrogen atoms. Preference is given to the carbon atoms in the positions 6, 9 and 10 being replaced by heteroatoms, in particular oxygen atoms.

The 2-phosphatricyclo[3.3.1.1{3,7}]decyl radical may be substituted by, for example, from 1 to 8, preferably from 1 to 4, substituents. In particular, it may bear substituents on one or more of its carbon atoms. Preference is given to one or more carbon atoms in the positions 1, 3, 5 and/or 7, in particular all carbon atoms in positions 1, 3, 5 and 7, bearing substituents which are preferably identical. Suitable substituents are, for example, halogen, alkyl, cycloalkyl, haloalkyl, aryl and or aralkyl. The carbon atoms in the positions 4 and/or 8 may bear one or two substituents, e.g. $C_1$–$C_4$-alkyl or halogen atoms, in particular fluorine atoms.

The radical R' is hydrogen or an organic radical having a molecular weight of up to 20 000, preferably up to 10 000, in particular up to 5 000, bound via a carbon atom, oxygen atom or nitrogen atom. The ligands used according to the present invention are monophosphines, monophosphinites or monophosphinamidites, i.e. the radical R' does not include a phosphorus atom. Possible radicals R' are, in particular, alkyl, e.g. alkyl having from 1 to 500 carbon atoms, which may be interrupted by nonadjacent heteroatoms, in particular oxygen atoms and/or nitrogen atoms; cycloalkyl, aryl, aralkyl, alkoxy, cycloalkoxy, aryloxy, aralkyloxy or acyl. Furthermore, R' may be a polymeric chain, e.g. $Z(CHR''CH_2O)_xR'''$ or $Z(CH_2CH_2NR'')_xR'''$, where Z is a bridge consisting of from 0 to 20 atoms of which adjacent atoms may be part of a saturated or unsaturated, carbocyclic or heterocyclic ring, and R" and R'" are each, independently of one another, hydrogen, alkyl, cycloalkyl, aryl, aralkyl or acyl and x is an integer from 1 to 240, preferably from 1 to 60. Examples of bridges Z are —CH$_2$—CH$_2$—O—, —CH$_2$—CH$_2$—N(R")—, —CH$_2$—CH$_2$— and the like.

Preferred ligands have the formula II,

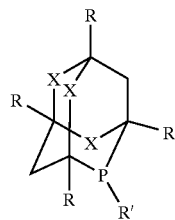

(II)

where

X are each, independently of one another, O or NR,

R are each, independently of one another, hydrogen, alkyl, cycloalkyl, haloalkyl, aryl or aralkyl and R' is hydrogen, alkyl, cycloalkyl, aryl, aralkyl, alkoxy, cycloalkoxy, aryloxy, aralkyloxy, alkylamino, di(alkyl)amino, cycloalkylamino, N-cycloalkyl-N-alkylamino, di(cycloalkyl)amino, arylamino, N-aryl-N-alkylamino, di(aryl)amino, aralkylamino, N-aralkyl-N-alkylamino, N-aralkyl-N-arylamino, di(aralkyl)amino, acyl or carbamoyl.

For the purposes of the present invention, the expressions employed (including those in compound nouns such as alkylamino and the like) have the following meanings:

"Alkyl": straight-chain or branched alkyl, preferably C$_1$–C$_{20}$-alkyl, in particular C$_1$–C$_8$-alkyl, particularly preferably C$_1$–C$_4$-alkyl; examples of alkyl groups are, in particular, methyl, ethyl, propyl, isopropyl, n-butyl, 2-butyl, s-butyl, t-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl;

"Cycloalkyl": preferably C$_5$–C$_7$-cycloalkyl such as cyclopentyl, cyclohexyl or cycloheptyl;

"Haloalkyl": preferably C$_1$–C$_4$-haloalkyl, i.e. a C$_1$–C$_4$-alkyl radical which is partially or fully substituted by fluorine, chlorine, bromine and/or iodine, e.g. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2,2-difluoroethyl, 2,2-dichloro-2-fluoroethyl, 2,2,2-trichloroethyl, pentafluoroethyl, 2-fluoropropyl, 3-fluoroproipyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

"Aryl": preferably C$_6$–C$_{16}$-aryl such as phenyl, tolyl, xylyl, mesityl, naphthyl, anthracenyl, phenanthrenyl, naphthacenyl; in particular phenyl or naphthyl;

"Aralkyl": preferably C$_7$–C$_{20}$-aralkyl, in particular phenyl-C$_1$–C$_4$-alkyl such as benzyl or phenethyl;

"Alkoxy": preferably C$_1$–C$_{20}$-alkoxy in which the alkyl group is preferably as defined above;

"Cycloalkyloxy": preferably C$_5$–C$_7$-cycloalkyloxy in which the cycloalkyl group is preferably as defined above;

"Aryloxy": preferably C$_7$–C$_{16}$-aryloxy in which the aryl group is preferably as defined above;

"Aralkyloxy": preferably C$_7$–C$_{20}$-aralkyloxy in which the aralkyl group is preferably as defined above; and "Acyl": preferably C$_1$–C$_{21}$-acyl such as formyl or C$_1$–C$_{20}$-alkylcarbonyl in which the alkyl group is preferably as defined above;

"Carbamoyl": preferably C$_1$–C$_{21}$-carbamoyl such as aminocarbonyl, C$_1$–C$_{20}$-alkylaminocarbonyl, C$_6$–C$_{16}$-arylaminocarbonyl or C$_7$–C$_{20}$-aralkylaminocarbonyl, each preferably having an alkyl, aryl or aralkyl group as defined above.

The radicals X are preferably O, NCH$_3$ or NH, in particular O.

The radicals R are each, independently of one another, particularly preferably C$_1$–C$_4$-alkyl, C$_1$–C$_4$-haloalkyl or phenyl, in particular methyl, t-butyl, trifluoromethyl or phenyl.

Particularly preferred ligands are selected from among 2-cyclohexyl-2-phospha-1,3,5,7-tetramethyl-6,9,10-trioxatricyclo [3.3.1.1{3,7}]decane, 2-phenyl-2-phospha-1,3,5,7-tetramethyl-6,9,10-trioxatricyclo[3.3.1.1{3,7}]decane, 2-t-butyl-2-phospha-1,3,5,7-tetramethyl-6,9,10-trioxatricyclo[3.3.1.1{3,7}]decane, 2-octyl-2-phospha-1,3,5,7-tetramethyl-6,9,10-trioxatricyclo [3.3.1.1{3,7}]decane and 2-phospha-1,3,5,7-tetramethyl-6,9,10-trioxatricyclo [3.3.1.1{3,7}] decane.

To prepare 6,9,10-trioxa-substituted ligands of the formula I, it is possible, for example, to react phosphine or a primary phosphine with a 1,3-diketone, e.g. 2,4-pentanedione or substituted 2,4-pentanediones such as perfluoro-2,4-pentanedione or 1,1,1,5,5,5-hexafluoro-2,4-pentanedione, in the presence of an acid catalyst. The compounds of the formula I are generally obtained in high purity and can be used directly without further purification. With regard to suitable reaction conditions, reference may be made to J. Am. Chem. Soc. 1961, Vol. 83, 3279–3282, and Chem. Comm. 1999 (10), 901–902.

In general, the catalysts or catalyst precursors used are converted under hydroformylation conditions into catalytically active species of the formula H$_x$M$_y$(CO)$_z$L$_q$, where M is ruthenium, rhodium, palladium, iridium and/or platinum, L is a ligand of the formula I and q, x, y, z are integers which depend on the valence and type of the metal. The complexes can, if desired, additionally contain further ligands which are preferably selected from among halides, amines, carboxylates, acetylacetonate, arylsulfonates and alkylsulfonates, olefins, dienes, cycloolefins, nitriles, nitrogen-containing heterocycles, aromatics and heteroaromatics, ethers, PF$_3$ and monodentate, bidentate and polydentate phosphine, phosphinite, phosphonite and phosphite ligands which do not correspond to the formula I.

In a preferred embodiment, the hydroformylation catalysts are prepared in situ in the reactor used for the hydroformylation reaction. However, if desired, the ligand-metal complexes can also be prepared separately and isolated by customary methods. For the in situ preparation, it is possible, for example, to react at least one ligand of the formula I, a compound or a complex of ruthenium, rhodium, palladium, iridium and/or platinum, optionally at least one further ligand and optionally an activating agent in an inert solvent with carbon monoxide and hydrogen under hydroformylation conditions.

Suitable rhodium compounds or complexes are, for example, rhodium(II) and rhodium(III) salts such as rhodium(III) chloride, rhodium(III) nitrate, rhodium(III) sulfate, potassium rhodium sulfate, rhodium(II) and rhodium(III) carboxylates such as rhodium(II) and rhodium (III) acetate, rhodium(III) oxide, salts of rhodic(III) acid, trisammoniumhexachlororhodate(III) etc. Rhodium complexes such as dicarbonylrhodium acetylacetonate, acetylacetonatobisethylenerhodium(I), etc., are also useful. Preference is given to using dicarbonylrhodium acetylacetonate or rhodium acetate.

Ruthenium salts or compounds are also suitable. Suitable ruthenium salts are, for example, ruthenium(III) chloride, ruthenium(IV), ruthenium(VI) or ruthenium(VIII) oxide, alkaline metal salts of ruthenium oxo acids, e.g. $K_2RuO_4$ or $KRuO_4$, or complexes such as $RuHCl(CO)(PPh_3)_3$. It is also possible to use carbonyls of ruthenium, e.g. dodecacarbonyltriruthenium or octadecacarbonylhexaruthenium, or mixed forms in which CO has partly been replaced by triorganophosphines, e.g. $Ru(CO)(PPh_3)_2$.

Suitable palladium, iridium and platinum compounds and complexes are known to those skilled in the art and are adequately described in the literature. The metal is preferably rhodium.

Suitable activating agents are, for example, Brönsted acids, Lewis acids such as $BF_3$, $AlCl_3$, $ZnCl_2$, and Lewis bases.

The molar ratio of ligand of the formula I to metal is generally in a range from about 50:1 to 1:1, preferably from 10:1 to 1:1.

Possible substrates for the process of the present invention are in principle all compounds which contain one or more ethylenically unsaturated double bonds. These include, for example, olefins such as α-olefins, internal linear and internal branched olefins. Suitable α-olefins are, for example, ethylene, propene, 1-butene, 1-pentene, 1-hexene, 1-heptene, 1-octene, 1-nonene, 1-decene, 1-undecene, 1-dodecene, etc.

Preferred internal linear olefins are $C_4$–$C_{20}$-olefins such as 2-butene, 2-pentene, 2-hexene, 3-hexene, 2-heptene, 3-heptene, 2-octene, 3-octene, 4-octene, etc.

Preferred internal branched olefins are $C_5$–$C_{20}$-olefins such as 2-methyl-2-butene, 2-methyl-2-pentene, 3-methyl-2-pentene.

Preferred starting materials are oligo($C_3$–$C_6$-alkenes) or poly($C_3$–$C_6$-alkenes), which are the oligomerization or polymerization products of $C_3$–$C_6$-alkenes such as propene, 1-butene, 2-butene, isobutene, pentene or hexenes. Preferred examples are propene trimer, butene dimer, butene trimer and hexene dimer and also polyisobutene having from 20 to 400 carbon atoms. The oligo($C_3$–$C_6$-alkenes), or poly ($C_3$–$C_6$-alkenes) are generally mixtures of essentially monounsaturated olefin isomers having a proportion of internal branched olefins.

Further suitable olefins for the hydroformylation process are vinylaromatics such as styrene, α-methylstyrene, 4-isobutylstyrene, etc.

Further suitable ethylenically unsaturated compounds are α,β-ethylenically unsaturated monocarboxylic and dicarboxylic acids, their esters, monoesters and amides, diacrylic acid, methacrylic acid, maleic acid, fumaric acid, crotonic acid, itaconic acid, methyl 3-pentenoate, methyl 4-pentenoate, methyl oleate, alkyl acrylates, alkyl methacrylates, unsaturated nitriles such as 3-pentenenitrile, 4-pentenenitrile, acrylonitrile, vinyl ethers such as vinyl methyl ether, vinyl ethyl ether, vinyl propyl ether, etc.

The process of the present invention is particularly advantageous when at least one linear compound having an internal double bond, i.e. a compound of the formula III, and/or at least one compound having an internal branched double bond, i.e. a compound of the formula IV,

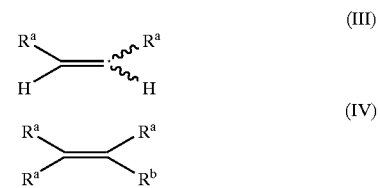

where $R^a$ are, independently of one another, radicals different from hydrogen, in particular alkyl, and $R^b$ is hydrogen or a radical different from hydrogen, in particular alkyl, is/are used as ethylenically unsaturated compound(s).

The sum of the numbers of carbon atoms in the radicals $R^a$ in the formula III is preferably from 2 to 30, in particular from 2 to 12. The sum of the numbers of carbon atoms of the radicals $R^a$ and $R^b$ in the formula IV is preferably from 3 to 30, in particular from 3 to 12. Preferred examples of such compounds are the internal linear and internal branched olefins mentioned above.

The hydroformylation reaction can be carried out continuously, semicontinuously or batchwise. Suitable reactors are known to those skilled in the art and are described, for example, in Ullmanns Enzyklopädie der Technischen Chemie, Volume 1, 3$^{rd}$ edition, 1951, p. 743ff.

Carbon monoxide and hydrogen are customarily used in the form of a mixture, known as synthesis gas. The molar ratio of carbon monoxide to hydrogen is generally from about 5:95 to 70:30, preferably from about 40:60 to 60:40. In particular, a molar ratio of carbon monoxide to hydrogen in the region of about 1:1 is used.

The temperature in the hydroformylation reaction is generally in a range from about 80 to 180° C., preferably from about 100 to 160° C. The reaction is generally carried out at the partial pressure of the reaction gas at the reaction temperature chosen. In general, the pressure is in a range from about 10 to 100 bar, in particular from 10 to 80 bar. The optimum temperature and the optimum pressure depend on the ethylenically unsaturated compound used. Thus, α-olefins are particularly preferably hydroformylated at from 80 to 120° C. and a pressure of from 10 to 40 bar. Internal and internal branched olefins are preferably hydroformylated at from 120 to 180° C. and a pressure of from 2 to 80 bar, with internal linear olefins being particularly preferably reacted at from 2 to 20 bar and internal branched olefins being particularly preferably reacted at from 40 to 80 bar.

The catalytically active ligand-metal complexes can be separated from the product mixture from the hydroformylation reaction by customary methods known to those skilled in the art and can generally, if necessary after work-up, be reused for the hydroformylation.

The hydroformylation can be carried out using solvents such as the high-boiling subsequent reaction products of the aldehydes which are formed in the hydroformylation. Suitable solvents likewise include aromatic hydrocarbons such as toluene and xylene, aliphatic hydrocarbons, ethers such as 2,5,8-trioxanonane (diglyme), diethyl ether and anisole, sulfones, such as sulfolane, or esters such as 3-hydroxy-2,2,4-trimethylpentyl 1-isobutyrate (Texanol).

The invention is illustrated by the following nonlimiting examples.

EXAMPLES

The ligands were synthesized in a manner analogous to the preparative method described in J. Am. Chem. Soc. 1961, Vol. 83, 3279+3282 and Chem. Colum. 1999 (10) 901–902. The butene dimer used in the examples was obtained by dimerization of a 1-butene- and 2-butene-containing $C_4$-hydrocarbon mixture over a heterogeneous, nickel-containing catalyst. It contained about 20% by weight of internal branched olefins. The abbreviation "acac" represents acetylacetonate; "L:M" is the molar ratio of ligand to metal.

Example 1

Hydroformylation of 1-octene using 2-cyclohexyl-2-phospha-1,3,5,7-tetramethyl-6,9,10-trioxatricyclo[3.3.1.1{3,7}]decane 0.9 mg of $Rh(CO)_2acac$ and 52 mg of 2-cyclohexyl-2-phospha-1,3,5,7-tetramethyl-6,9,10-trioxatricyclo [3.3.1.1{3,7}]decane (60 ppm of Rh, L:M=50:1) were weighed into a reaction vessel, dissolved in 3 g of toluene and treated at 100° C. with 10 bar of synthesis gas ($CO:H_2$=1:1). After 30 minutes, the reactor was depressurized, 3 g of 1-octene were then added and the mixture was hydroformylated at 100° C. and 10 bar for 4 hours. The conversion was 98%, and the aldehyde selectivity was 99%.

Example 2

Hydroformylation of butene dimer using 2-cyclohexyl-2-phospha-1,3,5,7-tetramethyl-6,9,10-trioxatricyclo[3.3.1.1{3,7}]decane 3 mg of $Rh(CO)_2acac$ and 32 mg of 2-cyclohexyl-2-phospha-1,3,5,7-tetramethyl-6,9,10-trioxatricyclo [3.3.1.1{3,7}]decane (60 ppm of Rh, L:M=10:1) were weighed into a reaction vessel, dissolved in 10 g of toluene and treated at 100° C. with 10 bar of synthesis gas ($CO:H_2$=1:1). After 30 minutes, the reactor was depressurized, 10 g of butene dimer were then added and the mixture was hydroformylated at 160° C. and 60 bar for 4 hours. The conversion was 94%, the nonanal selectivity was 99% and the nonanol selectivity was 1%.

Example 3

Hydroformylation of butene dimer using 2-cyclohexyl-2-phospha-1,3,5,7-tetramethyl-6,9,10-trioxatricyclo[3.3.1.1{3,7}]decane 3 mg of $Rh(CO)_2acac$ and 35 mg of 2-cyclohexyl-2-phospha-1,3,5,7-tetramethyl-6,9,10-trioxatricyclo [3.3.1.1{3,7}]decane (60 ppm of Rh, L:M=10:1) were weighed into a reaction vessel, dissolved in 10 g of toluene and treated at 100° C. with 10 bar of synthesis gas ($CO:H_2$=1:1). After 30 minutes, the reactor was depressurized, 10 g of butene dimer were then added and the mixture was hydroformylated at 140° C. and 60 bar for 4 hours. The conversion was 94%, the nonanal selectivity was 99% and the nonanol selectivity was 1%.

Example 4

Hydroformylation of 1-octene using 2-phospha-1,3,5,7-tetramethyl-6,9,10-trioxatricyclo[3.3.1.1{3,7}]decane 3 mg of $Rh(CO)_2acac$ and 125.6 mg of 2-phospha-1,3,5,7-tetramethyl-6,9,10-trioxatricyclo [3.3.1.1{3,7}] decane (60 ppm of Rh, L:M=50:1) were dissolved separately in a total of 10 g of toluene, the solutions were mixed and the mixture was treated at 100° C. with 10 bar of synthesis gas ($CO:H_2$=1:1). After 30 minutes, the reactor was depressurized, 10 g of 1-octene were then added and the mixture was hydroformylated at 100° C. and 10 bar for 4 hours. The conversion was 29%, and the aldehyde selectivity was 100%.

Example 5

Hydroformylation of butene dimer using 2-phospha-1,3,5,7-tetramethyl-6,9,10-trioxatricyclo[3.3.1.1{3,7}]decane 3 mg of $Rh(CO)_2acac$ and 25.1 mg of 2-phospha-1,3,5,7-tetramethyl-6,9,10-trioxatricyclo [3.3.1.1{3,7}] decane (60 ppm of Rh, L:M=10:1) were dissolved separately in a total of 10 g of toluene, the solutions were mixed and the mixture was treated at 100° C. with 10 bar of synthesis gas ($CO:H_2$=1:1). After 30 minutes, the reactor was depressurized, 10 g of butene dimer were then added and the mixture was hydroformylated at 160° C. and 80 bar for 4 hours. The conversion was 88%, the nonanal selectivity was 89% and the nonanol selectivity was 2%.

Example 6

Hydroformylation of 1-octene using 2-octyl-2-phospha-1,3,5,7-tetramethyl-6,9,10-trioxatricyclo[3.3.1.1{3,7}]decane 0.75 mg of $Rh(CO)_2acac$ and 28.6 mg of 2-octyl-2-phospha-1,3,5,7-tetramethyl-6,9,10-trioxatricyclo [3.3.1.1{3,7}]decane (60 ppm, L:M=30:1) were dissolved separately in a total of 2.5 g of toluene, the solutions were mixed and the mixture was treated at 100° C. with 10 bar of synthesis gas ($CO:H_2$=1:1). After 30 minutes, the reactor was depressurized, 2.5 g of 1-octene were then added and the mixture was hydroformylated at 100° C. and 10 bar for 4 hours. The conversion was 98%, the aldehyde selectivity was 100% and the linearity was 56%.

Example 7

Hydroformylation of butene dimer using 2-cyclohexyl-2-phospha-1,3,5,7-tetramethyl-6,9,10-trioxatricyclo[3.3.1.1{3,7}]decane 3 mg of $Rh(CO)_2acac$ and 6.9 mg of 2-cyclohexyl-2-phospha-1,3,5,7-tetramethyl-6,9,10-trioxatricyclo [3.3.1.1{3,7}]decane (60 ppm of Rh, L:M=

2:1) were dissolved separately in a total of 10 g of toluene, the solutions were mixed and the mixture was treated at 100° C. with 10 bar of synthesis gas ($CO:H_2=1:1$). After 30 minutes, the reactor was depressurized, 10 g of butene dimer were then added and the mixture was hydroformylated at 140° C. and 60 bar for 4 hours. The conversion was 74%, and the nonanal selectivity was 100%.

Example 8

Hydroformylation of butene dimer using 2-octyl-2-phospha-1,3,5,7-tetramethyl-6,9,10-trioxatricyclo [3.3.1.1{3,7}]decane 3 mg of $RH(CO)_2acac$ and 38.1 mg of 2-octyl-2-phospha-1,3,5,7-tetramethyl-6,9,10-trioxatricyclo [3.3.1.1{3,7}]decane (60 ppm of Rh, L:M=10:1) were dissolved separately in a total of 10 g of toluene, the solutions were mixed and the mixture was treated at 100° C. with 10 bar of synthesis gas ($CO:H_2=1:1$). After 30 minutes, the reactor was depressurized, 10 g of butene dimer were then added and the mixture was hydroformylated at 140° C. and 40 bar for 4 hours. The conversion was 48%, and the nonanal selectivity was 100%.

Example 9

Hydroformylation of butene dimer using 2-octyl-2-phospha-1,3,5,7-tetramethyl-6,9,10-trioxatricyclo [3.3.1.1{3,7}]decane 3 mg of $RH(CO)_2acac$ and 38.1 mg of 2-octyl-2-phospha-1,3,5,7-tetramethyl-6,9,10-trioxatricyclo [3.3.1.1{3,7}]decane (60 ppm of Rh, L:M=10:1) were dissolved separately in a total of 10 g of toluene, the solutions were mixed and the mixture was treated at 100° C. with 10 bar of synthesis gas ($CO:H_2=1:1$). After 30 minutes, the reactor was depressurized, 10 g of butene dimer were then added and the mixture was hydroformylated at 140° C. and 60 bar for 4 hours. The conversion was 74%, the nonanal selectivity was 99% and the nonanol selectivity was 1%.

Example 10

Hydroformylation of butene dimer using 2-octyl-2-phospha-1,3,5,7-tetramethyl-6,9,10-trioxatricyclo [3.3.1.1{3,7}]decane 3 mg of $RH(CO)_2acac$ and 38.1 mg of 2-octyl-2-phospha-1,3,5,7-tetramethyl-6,9,10-trioxatricyclo [3.3.1.1{3,7}]decane (60 ppm of Rh, L:M=10:1) were dissolved separately in a total of 10 g of toluene, the solutions were mixed and the mixture was treated at 100° C. with 10 bar of synthesis gas ($CO:H_2=1:1$). After 30 minutes, the reactor was depressurized, 10 g of butene dimer were then added and the mixture was hydroformylated at 140° C. and 80 bar for 4 hours. The conversion was 88%, the nonanal selectivity was 99% and the nonanol selectivity was 1%.

Example 11

Hydroformylation of butene dimer using 2-octyl-2-phospha-1,3,5,7-tetramethyl-6,9,10-trioxatricyclo [3.3.1.1{3,7}]decane 2 mg of $RH(CO)_2acac$ and 38.1 mg of 2-octyl-2-phospha-1,3,5,7-tetramethyl-6,9,10-trioxatricyclo [3.3.1.1{3,7}]decane (60 ppm of Rh, L:M=10:1) were dissolved separately in a total of 10 g of toluene, the solutions were mixed and the mixture was treated at 100° C. with 10 bar of synthesis gas ($CO:H_2=1:1$). After 30 minutes, the reactor was depressurized, 10 g of butene dimer were then added and the mixture was hydroformylated at 160° C. and 40 bar for 4 hours. The conversion was 44%, the nonanal selectivity was 98% and the nonanol selectivity was 2%.

Example 12

Hydroformylation of butene dimer using 2-octyl-2-phospha-1,3,5,7-tetramethyl-6,9,10-trioxatricyclo [3.3.1.1{3,7}]decane 3 mg of $RH(CO)_2acac$ and 38.1 mg of 2-octyl-2-phospha-1,3,5,7-tetramethyl-6,9,10-trioxatricyclo [3.3.1.1{3,7}]decane (60 ppm of Rh, L:M=10:1) were dissolved separately in a total of 10 g of toluene, the solutions were mixed and the mixture was treated at 100° C. with 10 bar of synthesis gas ($CO:H_2=1:1$). After 30 minutes, the reactor was depressurized, 10 g of butene dimer were then added and the mixture was hydroformylated at 160° C. and 60 bar for 4 hours. The conversion was 72%, the nonanal selectivity was 94%, the nonanol selectivity was 3% and the proportion of aldol was 3%.

Example 13

Hydroformylation of butene dimer using 2-octyl-2-phospha-1,3,5,7-tetramethyl-6,9,10-trioxatricyclo [3.3.1.1{3,7}]decane 3 mg of $RH(CO)_2acac$ and 38.1 mg of 2-octyl-2-phospha-1,3,5,7-tetramethyl-6,9,10-trioxatricyclo [3.3.1.1{3,7}]decane (60 ppm of Rh, L:M=10:1) were dissolved separately in a total of 10 g of toluene, the solutions were mixed and the mixture was treated at 100° C. with 10 bar of synthesis gas ($CO:H_2=1:1$). After 30 minutes, the reactor was depressurized, 10 g of butene dimer were then added and the mixture was hydroformylated at 160° C. and 80 bar for 4 hours. The conversion was 83%, the nonanal selectivity was 89%, the nonanol selectivity was 5% and the proportion of aldol was 6%.

Comparative Example A

Hydroformylation of butene dimer using 1,3-P,P'-di(2-phospha-1,3,5,7-tetramethyl-6,9,10-trioxatricyclo [3.3.1.1{3,7}]decyl)-propane 3 mg of $Rh(CO)_2acac$ and 274 mg of 1,3-P,P'-di(2-phospha-1,3,5,7-tetramethyl-6,9,10-trioxatricyclo [3.3.1.1{3,7}]decyl)propane (60 ppm of Rh, L:M=50:1) were weighed into a reaction vessel, dissolved in 10 g of toluene and treated at 100° C. with 10 bar of synthesis gas ($CO:H_2=1:1$). After 30 minutes, the reactor was depressurized, 10 g of butene dimer were then added and the mixture was hydroformylated at 160° C. and 80 bar for 4 hours. The conversion was 2%, and the nonanal selectivity was 100%.

Comparative Example B

Hydroformylation of butene dimer using 1,3-P,P'-di(2-phospha-1,3,5,7-tetramethyl-6,9,10-trioxatricyclo [3.3.1.1{3,7}]decyl) propane Comparative example A was repeated using an L:M of 10:1. This gave the same result as comparative example A.

Comparative Example C

Hydroformylation of 2-octene using 1,3-P,P'-di(2-phospha-1,3,5,7-tetramethyl-6,9,10-trioxatricyclo[3.3.1.1{3,7}]decyl)propane 3 mg of $Rh(CO)_2acac$ and 274 mg of 1,3-P,P'-di(2-phospha-1,3,5,7-tetramethyl-6,9,10-trioxatricyclo [3.3.1.1{3,7}]decyl)propane (60 ppm of Rh, L:M=50:1) were weighed into a reaction vessel, dissolved in 10 g of toluene and treated at 100° C. with 10 bar of synthesis gas ($CO:H_2$=1:1). After 30 minutes, the reactor was depressurized, 10 g of 2-octene were then added and the mixture was hydroformylated at 160° C. and 80 bar for 4 hours. The conversion was 14%, and the aldehyde selectivity was 79%.

Comparative example D

Hydroformylation of butene dimer using triphenylphosphine 7.5 g of $Rh(CO)_2acac$ and 157 mg of triphenylphosphine (60 ppm of Rh, L:M=20:1) were dissolved separately in a total of 25 g of toluene, the solutions were mixed and the mixture was treated at 100° C. with 10 bar of synthesis gas ($CO:H_2$=1:1). After 30 minutes, the reactor was depressurized, 25.1 g of butene dimer were then added and the mixture was hydroformylated at 160° C. and 60 bar for 4 hours. The conversion was 9%, and the nonanal selectivity was 47%.

I claim:

1. A process for the hydroformylation of ethylenically unsaturated compounds, in which at least one ethylenically unsaturated compound is reacted with carbon monoxide and hydrogen in the presence of a ligand-metal complex of ruthenium, rhodium, palladium, iridium and/or platinum, where the ligand-metal complex comprises a monophosphine, monophosphinite or monophosphineamidite wherein the ligand has the formula II

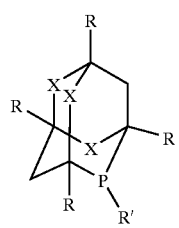

(II)

where
    X are each, independently of one another O or NR,
    R are each, independently of one another, hydrogen, alkyl, cycloalkyl, haloalkyl, aryl or aralkyl and
    R' is hydrogen, alkyl, cycloalkyl, aryl, aralkyl, alkoxy, cycloalkoxy, aryloxy, aralkyloxy, alkylamino, di(alkyl)amino, cycloalkylamino, N-cycloalkyl-N-alkylamino, di(cycloalkyl) amino, arylamino, N-aryl-N-alkylamino, di(aryl)amino, aralkylamino, N-aralkyl-N-alkylamino, N-aralkyl-N-arylamino, di(aralkyl)amino, acyl or carbamoyl.

2. A process as claimed in claim 1, wherein the radicals R are each, independently of one another, methyl, t-butyl, trifluoromethyl or phenyl.

3. A process as claimed in claim 2, wherein the ligand is selected from among 2-cyclohexyl-2-phospha-1,3,5,7-tetramethyl-6,9,10-trioxatricyclo[3.3.1.1{3,7}]decane, 2-octyl-2-phospha-1,3,5,7-tetramethyl-6,9,10-trioxatricyclo[3.3.1.1 {3,7}]decane, 2-phenyl-2-phospha-1,3,5,7-tetramethyl-6,9,10-trioxatricyclo[3.3.1.1 {3,7}]decane, 2-t-butyl-2-phospha-1,3,5,7-tetramethyl-6,9,10-trioxatricyclo[3.3.1.1 {3,7}]decane 2-phospha-1,3,5,7-tetramethyl-6,9,10-trioxatricyclo [3.3.1.1 {3,7}]decane.

4. A process as claimed in claim 1, wherein at least one compound of the formula III or IV,

(III)

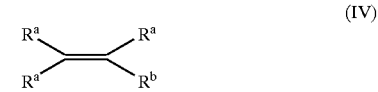

(IV)

where $R^a$ are, independently of one another, radicals different from hydrogen and
    $R^b$ is hydrogen or a radical different from hydrogen, is used as ethylenically unsaturated compound.

5. A process as claimed in claim 4, wherein an oligo ($C_3$–$C_5$-alkene) or poly($C_3$–$C_6$-alkene) is used as ethylenically unsaturated compound.

6. A ligand-metal complex comprising a metal selected from among ruthenium, rhodium, palladium, iridium and/or platinum and at least one monophosphine, monophosphinite or monophosphinamidite wherein the ligand has the formula II

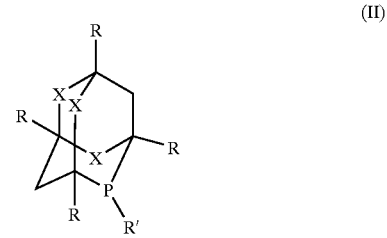

(II)

where

X are each, independently of one another O or NR,

R are each, independently of one another, hydrogen, alkyl, cycloalkyl, haloalkyl, aryl or aralkyl and R' is hydrogen, alkyl, cycloalkyl, aryl, aralkyl, alkoxy, cycloalkoxy, aryloxy, aralkyloxy, alkylamino, di(alkyl) amino, cycloalkylamino, N-cycloalkyl-N alkylamino, di(cycloalkyl) amino, arylamino, N-aryl-N-alkylamino, di(aryl)amino, aralkylamino, N-aralkyl-N-alkylamino, N-aralkyl-N-arylamino, di(aralkyl)amino, acyl or carbamoyl.

* * * * *